(12) United States Patent
Hannan et al.

(10) Patent No.: US 9,044,555 B2
(45) Date of Patent: Jun. 2, 2015

(54) EXTRACORPOREAL BLOOD CIRCUIT FOR CARDIOPULMONARY BYPASS

(75) Inventors: Robert L. Hannan, Pinecrest, FL (US);
Jorge W. Ojito, Miami, FL (US);
Redmond Paul Burke, Miami, FL (US)

(73) Assignee: MIAMI CHILDREN'S HOSPITAL RESEARCH INSTITUTE, Miami, FL (US)

( * ) Notice: Subject to any disclaimer, the term of this patent is extended or adjusted under 35 U.S.C. 154(b) by 441 days.

(21) Appl. No.: 12/853,084

(22) Filed: Aug. 9, 2010

(65) Prior Publication Data

US 2011/0040229 A1  Feb. 17, 2011

Related U.S. Application Data

(60) Provisional application No. 61/233,281, filed on Aug. 12, 2009.

(51) Int. Cl.
*A61M 37/00* (2006.01)
*A61M 1/36* (2006.01)

(52) U.S. Cl.
CPC ........... *A61M 1/3666* (2013.01); *A61M 1/3667* (2014.02)

(58) Field of Classification Search
None
See application file for complete search history.

(56) References Cited

U.S. PATENT DOCUMENTS

| | | | |
|---|---|---|---|
| 3,882,861 A * | 5/1975 | Kettering et al. | 604/66 |
| 5,823,986 A * | 10/1998 | Peterson | 604/6.09 |
| 6,017,493 A * | 1/2000 | Cambron et al. | 422/44 |
| 6,315,751 B1 | 11/2001 | Cosgrove et al. | |
| 6,524,267 B1 | 2/2003 | Gremel et al. | |
| 6,547,775 B1 * | 4/2003 | Blyakhman | 604/505 |
| 6,579,496 B1 * | 6/2003 | Fausset et al. | 422/44 |
| 7,541,000 B2 * | 6/2009 | Stringer et al. | 422/45 |
| 2005/0118059 A1 * | 6/2005 | Olsen et al. | 604/4.01 |
| 2006/0089586 A1 * | 4/2006 | Kaus et al. | 604/4.01 |
| 2008/0027368 A1 * | 1/2008 | Kollar et al. | 604/6.14 |
| 2008/0146995 A1 * | 6/2008 | Smisson et al. | 604/67 |
| 2008/0154170 A1 * | 6/2008 | Lannoy | 604/6.09 |

FOREIGN PATENT DOCUMENTS

| | | |
|---|---|---|
| EP | 1 557 186 A1 | 7/2005 |
| JP | 2006/280395 A | 10/2006 |
| JP | 2007/518503 A | 7/2007 |
| JP | 2008/517651 A | 5/2008 |
| WO | WO 02/064013 | 8/2002 |
| WO | WO 2006/047147 A1 | 5/2006 |

* cited by examiner

*Primary Examiner* — Jackie T Ho
*Assistant Examiner* — Eric Bryant
(74) *Attorney, Agent, or Firm* — Saliwanchik, Lloyd & Eisenschenk

(57) ABSTRACT

The subject invention provides an improved bypass circuit for use in adult and especially pediatric cardiac surgery. The auto regulating capability of this circuit design simplifies its operation and combines the benefits of both VAVD and KAVD systems while eliminating the need for multiple blood pumps. Advantageously, this system occupies less space than existing systems, requires the use of less blood, reduces the contact between blood and tubing, reduces damage to blood cells, eliminates the need for multiple blood pumps and also reduces the incidence of gaseous emboli.

16 Claims, 2 Drawing Sheets

EXTRACORPOREAL BLOOD CIRCUIT FOR CARDIOPULMONARY BYPASS

CROSS-REFERENCE TO A RELATED APPLICATION

This application claims the benefit of U.S. provisional application Ser. No. 61/233,281, filed Aug. 12, 2009, which is incorporated herein by reference in its entirety.

BACKGROUND

In the field of medicine, treatments suitable for use with adult patients are not always similarly applicable for use with pediatric patients. One realm where this is particularly true is in the area of cardiopulmonary support. The field of mechanical circulatory support is evolving rapidly. However, devices that augment or replace cardiac function for adult patients cannot necessarily be used easily, or successfully, with pediatric patients, particularly with neonatal patients.

Conventional cardiopulmonary bypass (CPB) uses an extracorporeal blood circuit that is coupled between arterial and venous cannulae and includes at least a venous drainage line and an arterial return line, a blood reservoir, one pump to propel the blood in the circuit and multiple pumps to recover shed blood from the operative field and return it to the circuit via the reservoir, an oxygenator, bubble traps and or blood filters, blood flow probe, blood gas analyzers, blood transporting tubing or "lines," ports, and valves interconnecting these components.

Traditional bypass systems utilize gravity to drain venous blood from the patient and require the use of large diameter venous cannulae and large diameter tubing in order to maintain adequate drainage. More recent techniques employ one of two methods to actively aspirate blood from the patient and augment venous return. One approach, Kinetic assisted venous drainage (KAVD), uses a centrifugal pump; and the other, Vacuum assisted venous drainage (VAVD), utilizes standard wall suction.

All of these techniques, although effective, have a particular set of limitations; including:

(1) Gravity drainage circuits have large circuit priming volumes and depend on large diameter venous cannulae thwarting its use in both pediatric and minimally invasive surgery.

(2) KAVD utilizes a centrifugal pump in the venous line that can become air-locked and ineffective during a procedure if a large amount of venous air is present. To address this limitation the use of a bubble trap in the venous line pre-pump has been described. This configuration requires that the cardiotomy reservoir or transfusion bags be attached to the venous line pre-bubble trap making the circuit much more difficult to manage. As a result KAVD systems are currently mostly utilized in adult bypass surgery when minimal blood loss is expected and the use of a cardiotomy reservoir is not necessary. Unlike adult surgery the majority of pediatric surgery takes place inside the heart and is associated with a large amount of blood loss, prohibiting the elimination of the blood reservoir.

(3) VAVD is currently the preferred CPB system of choice in pediatrics and is accomplished by connecting the venous line to a sealed hard shell cardiotomy reservoir to which a regulated vacuum source has been applied. This type of system increases air to blood interface and decreases the amount of time air bubbles have to settle out of circulation while in the reservoir, exacerbating arterial line emboli.

(4) All three of these circuits in use today are dependent on the use of multiple roller pumps to return shed blood back into the circulation from the surgical field when needed. Roller pumps require the use of tubing connecting the operative field to the blood reservoir, increasing the amount of blood held out of circulation during the procedure.

The standard technique during CPB support continues to be the use of venoarterial bypass with a membrane oxygenator, providing both hemodynamic and pulmonary support. However the current technology and design of the conventional CPB circuits are not optimal for use especially in pediatric patients. The shortcomings of the CPB circuits include large prime volumes, use of pumps that damage blood cells, extensive contact of the blood with tubing, difficulty controlling bubbles, failure to conserve blood, and difficulty due to bulky equipment.

The pumping mechanism of CPB devices pump the poorly oxygenated blood into the artificial lung where carbon dioxide is removed from the blood and oxygen is provided. Before the blood is oxygenated it can pass through a heat exchanger to raise or lower the blood temperature in order to manage patient body temperature. The oxygenated, warmed/cooled blood is then pumped back to the patient.

As noted above, disadvantages of CPB include large blood volume requirements, damage to blood cells, difficulty in managing fluid volume, increased gaseous emboli and the need to use multiple blood pumps.

Thus, the need remains for an extracorporeal blood circuit advantageously created with the pediatric or neonate patient in mind. Ideally, the size of the extracorporeal circuit would be reduced to lower the required volume to prime the circuit and to reduce the undesirable contact between the blood and the components of the circuit. In addition, the need remains for improved blood flow and blood pumping mechanisms in the extracorporeal circuits to further lessen the current problems of blood-air mixing and hemolysis of red blood cells.

BRIEF SUMMARY

The subject invention provides an improved bypass circuit for use in adult and pediatric cardiac surgery. Advantageously, this system occupies less space than existing systems, requires the use of less blood, reduces the contact between blood and tubing, eliminates the need for multiple blood pumps, reduces damage to blood cells, simplifies blood flow and fluid management and also reduces the incidence of arterial line emboli.

BRIEF DESCRIPTION OF DRAWINGS

In order that a more precise understanding of the above-recited invention can be obtained, a more particular description of the invention briefly described above will be rendered by reference to specific embodiments thereof that are illustrated in the appended drawings. It should also be understood that the drawings presented herein may not be drawn to scale and that any reference or implication of dimensions in the drawings or the following description are specific to the embodiments disclosed. Any variations of these dimensions that will allow the subject invention to function for its intended purpose are considered to be within the scope of the subject invention. Thus, understanding that these drawings depict only specific embodiments of the invention and are not therefore to be considered as limiting in scope, the invention will be described and explained with additional specificity and detail through the use of the accompanying drawings in which.

DETAILED DISCLOSURE

Figure 1:
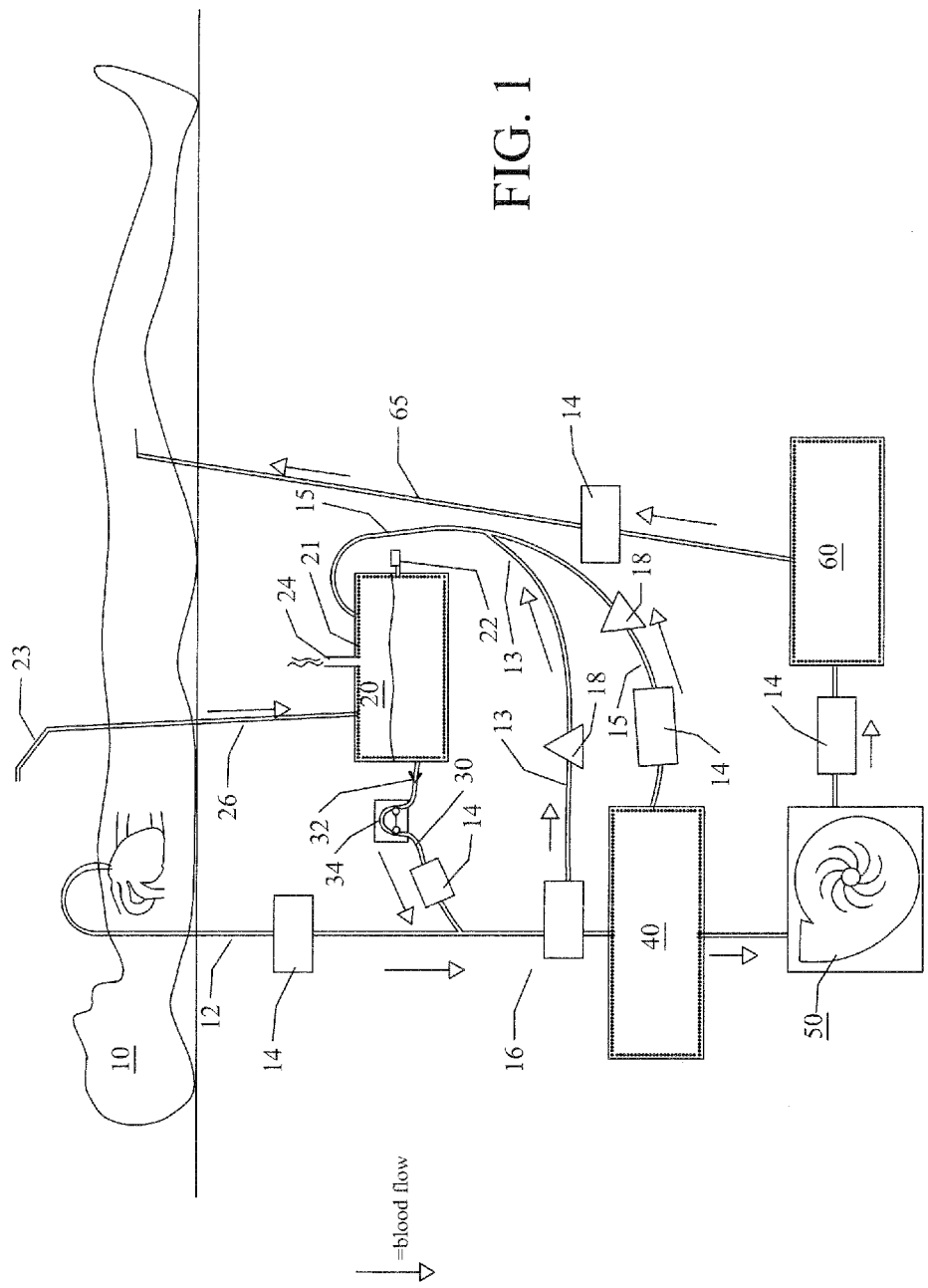
FIG. 1 is a schematic drawing of one embodiment of the system of the subject invention.

The subject invention provides new and advantageous mechanical circulatory support devices and methods. More specifically, the subject invention provides extracorporeal life support (ECLS) devices, capable of providing extracorporeal cardiopulmonary support for adult, pediatric and neonatal cardiac patients.

The subject invention provides an improved bypass circuit for use in adult and pediatric cardiac surgery. Advantageously, this system occupies less space than existing systems, requires the use of less blood, reduces the contact between blood and tubing, eliminates the need for multiple blood pumps, reduces damage to blood cells, simplifies blood flow and fluid management and also reduces the incidence of arterial line emboli.

The term "patient" as used herein, describes an animal, including mammals, to which the systems and methods of the present invention are applied. Mammalian species that can benefit from the disclosed systems and methods include, but are not limited to, apes, chimpanzees, orangutans, humans, monkeys; domesticated animals (e.g., pets) such as dogs, cats, guinea pigs, hamsters; veterinary uses for large animals such as cattle, horses, goats, sheep; and any wild animal for veterinary or tracking purposes.

The terms "surgeon" or "physician" as used in the subject invention are merely for literary convenience. The terms should not be construed as limiting in any way. The devices, apparatuses, methods, techniques and/or procedures of the subject invention could be utilized by any person desiring or needing to do so and having the necessary skill and understanding of the invention.

Also, as used herein, and unless otherwise specifically stated, the terms "operable communication" and "operably connected" mean that the particular elements are connected in such a way that they cooperate to achieve their intended function or functions. The "connection" may be direct, or indirect, physical or remote.

In addition, references to "first", "second", and the like (e.g., first and second pressure-detector), as used herein, and unless otherwise specifically stated, are intended to identify a particular feature of which there are at least two. However, these references are not intended to confer any order in time, structural orientation, or sidedness (e.g., left or right) with respect to a particular feature.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

With reference to the attached figures, which show two embodiments of the system of the subject invention, it can be seen that the subject invention comprises an extracorporeal cardiopulmonary life support circuit. One advantage of the system of the subject invention is that it occupies a small area and can be located near the head of a patient. For example, the system can be mounted on a table. Because less tubing is used, the system requires less blood, which is important in the case of pediatric surgery, where available blood volume can be very limited. Also, contact between the blood and the tubing is reduced, thereby reducing the likelihood and extent of deleterious antigenic interactions.

Advantageously, the system of the subject invention operates without the need for gravity drainage. The pressure and flow of blood within the system of the ECLS system of the subject invention can be controlled by pumps and suction. Pumps within the system force blood to move through certain regions of the system. Blood can also be moved by creating negative pressure. Further, one or more pumps (and/or the negative pressure generating device) within the system can be operably connected to, and controlled by, one or more pressure-detectors 14 within the system line. Undesirable changes in pressure within the system can cause the one or more pressure-detectors to alter the operation of the pump and/or negative pressure generating device.

In the system of the subject invention, blood is carried from the patient 10 through, for example, a cannula placed within the right atrium or vena cava. A venous line 12 carries blood from the patient into the system of the subject invention. In one embodiment, a first pressure-detector 14 is located in-line with the venous line 12, as shown, for example, in FIG. 1. In an embodiment shown in FIG. 1, the line 12 continues past the first pressure-detector 14, carrying blood into a bubble detector 16.

Figure 2:
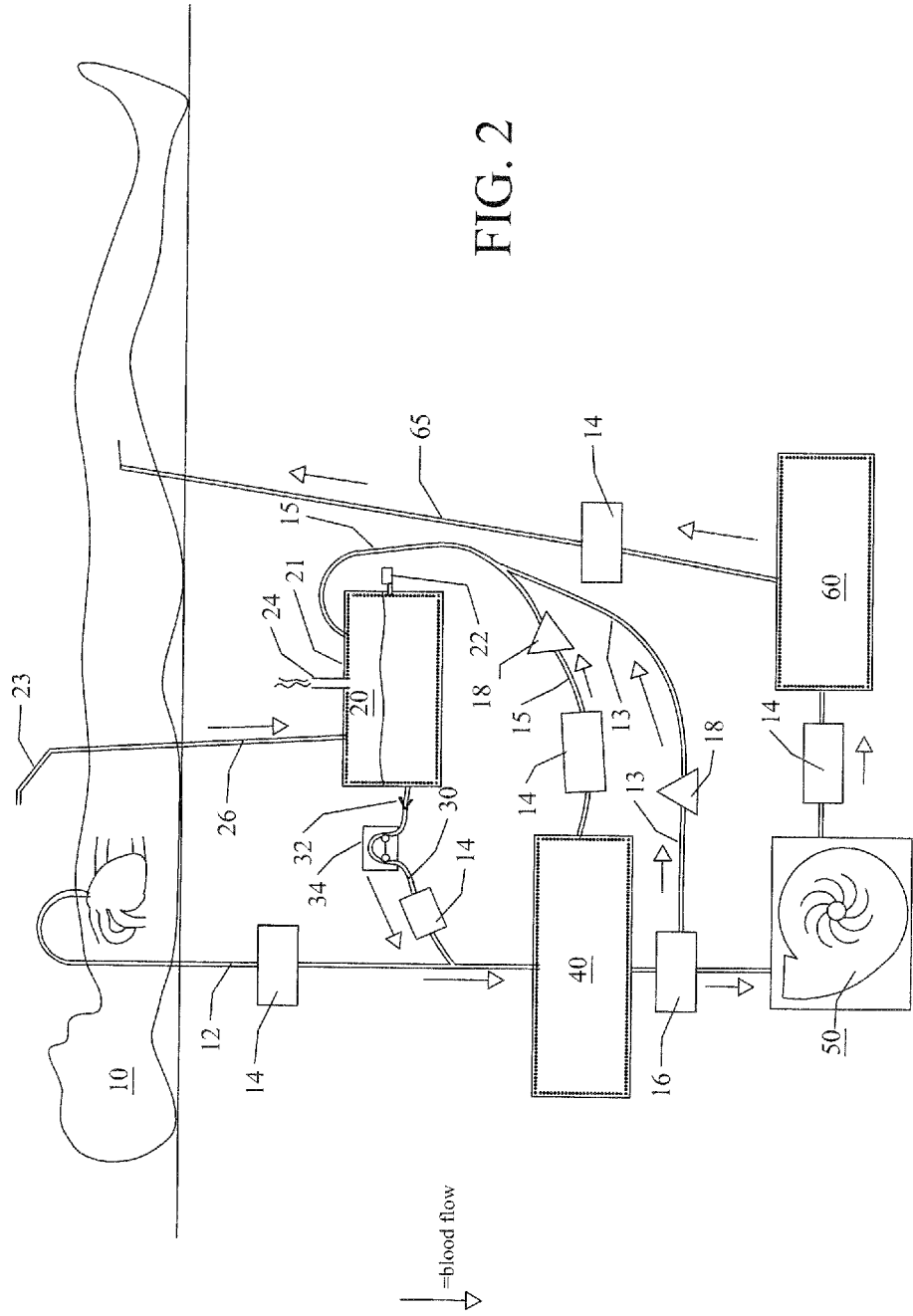
FIG. 2 is a schematic drawing of one embodiment of the system of the subject invention.

The bubble detector 16 detects bubbles within the line 12. After passing through the bubble detector, the blood is allowed to proceed into a bubble trap 40 where bubbles are removed, or is directed to a reservoir 20 through a line 13. Advantageously, the bubble trap often also acts as a filter to remove particulate emboli that may be present. In another embodiment, as shown, for example, in FIG. 2, the bubble detector is located past the bubble trap, and blood can be directed to the reservoir 20 through line 13. In one embodiment, an occluder 18 can be used to direct the bubble-containing blood directly to the reservoir from where it will then exit and ultimately pass through the bubble trap. The occluder clamp will typically remain open until a bubble detector located in the line exiting the bubble trap determines that no further air or bubbles are present in the line.

Within the blood reservoir 20, blood is stored temporarily. Also collected within the blood reservoir 20 is blood that may be aspirated by a suction device 23 from the site of surgery. The figures illustrate examples of a blood reservoir 20 into which is delivered bubble-containing blood from the venous line and bubble trap/filter as well as blood suctioned from the surgical field.

Blood leaves the reservoir through a reservoir return line 30. In-line with the reservoir return line 30 can be a roller pump 34. The roller pump 34 pulls blood from the reservoir 20 through the reservoir return line 30, as shown, for example, in FIGS. 1 and 2. To prevent backflow into the reservoir, the reservoir return line can also include a one-way valve 32, either before or after the roller pump 34. Further, to prevent the roller pump from operating when the blood level in the reservoir is below the desired level, an adjustable blood level detector 22 can be operably connected to the reservoir and the roller pump. When the blood level detector 22 determines that the blood level within the reservoir is too low, it can direct the roller pump to cease, or at least reduce, operation, until such time as the blood level rises.

The reservoir 20 of the subject invention can be subjected to negative pressure that can be adjusted via a vacuum regulator 24. The reservoir can also be self-regulating 21 in order to prevent excessive positive or negative pressure. The reservoir suction inlets (26, for example) can be independently adjustable to the desired amount of negative pressure desired.

This allows the clinician to regulate the amount of suction that is applied to each line returning blood to the reservoir, thereby eliminating the need for multiple blood pumps.

As mentioned above, the ECLS system of the subject invention can include one or more in-line pressure detectors. As shown in the Figures, a pressure detector 14 can also, or instead, be located in-line following the roller pump. Assuming that pressure within the reservoir return line 30 is at an adequate level, blood will be returned, from the reservoir, to the venous line 12, preferably before a bubble detector 16.

Blood and bubbles that are not directed to the reservoir 20 are allowed to flow into a bubble trap 40. The bubble trap removes bubbles and debris from the blood. In one embodiment, a line 15 transfers blood from the bubble trap to the reservoir. De-bubbled blood is pulled from the bubble trap by a pump 50. In one embodiment, this blood passes through a bubble detector 16. If bubbles are detected, the blood is returned to the bubble trap 40 or is sent to the reservoir 20.

In a particular embodiment, an impeller or centrifugal pump 50 is utilized to remove blood from the bubble trap. Advantageously, impeller or centrifugal pumps do not produce an increase in arterial limb pressure, which reduces the risk of circuit rupture if a distal occlusion occurs. In addition, the use of a centrifugal pump eliminates the need for gravity drainage, thereby permitting shorter tubing lengths and allowing for greater portability. Centrifugal pumps also cause less damage to red blood cells.

The centrifugal pump 50 directs blood to a blood oxygenator/heat exchanger 60 where it is prepared for transport via the arterial line 65 back to the patient.

It should be understood that the examples and embodiments described herein are for illustrative purposes only and that various modifications or changes in light thereof will be suggested to persons skilled in the art and are to be included within the spirit and purview of this application.

What is claimed is:

1. A pediatric extracorporeal life support device, comprising:
   a venous line to carry blood from a patient;
   a first pressure detector in line with the venous line;
   a bubble detector in line with the venous line;
   a bubble trap in line with the venous line;
   a blood reservoir for receiving blood that has passed through the bubble detector;
   a reservoir return line connecting the blood reservoir to the venous line and configured to return blood to the venous line up-line from the bubble detector;
   a first pump in line with the reservoir return line, between the blood reservoir and the venous line;
   an adjustable blood level detector operably connected to the blood reservoir and the first pump and configured to detect a blood level within the blood reservoir;
   a second pump down-line from the bubble trap;
   a second pressure detector down-line from the second pump;
   an oxygenator down-line from the second pressure detector; and
   an arterial line for transporting blood from the oxygenator back to the patient,
   wherein the first pump is capable of pumping blood from the blood reservoir to the venous line, and
   wherein the adjustable blood level detector is configured such that, when the adjustable blood level detector determines that the blood level within the blood reservoir is below a threshold value, the adjustable blood level detector directs the first pump to reduce or cease operation until the blood level within the blood reservoir reaches an acceptable level.

2. The pediatric extracorporeal life support device according to claim 1, wherein the second pump is an impeller or centrifugal pump.

3. The pediatric extracorporeal life support device according to claim 1, wherein the oxygenator also serves as a heat exchanger capable of heating the blood.

4. The pediatric extracorporeal life support device according to claim 1, further comprising an occluder clamp on a line connecting the bubble detector and the blood reservoir.

5. The pediatric extracorporeal life support device according to claim 1, wherein the blood reservoir comprises a vacuum regulator that is capable of adjusting the pressure of the blood reservoir.

6. The pediatric extracorporeal life support device according to claim 1, wherein the blood reservoir is self-regulating.

7. The pediatric extracorporeal life support device according to claim 1, further comprising a suction device line connected to the blood reservoir, wherein the blood reservoir is capable of receiving blood collected by a suction device and provided through the suction device line during a surgical procedure.

8. A method of oxygenating blood from a pediatric patient, the method comprising:
   directing the blood through an extracorporeal life support extracorporeal life support device, wherein the device comprises:
   a venous line to carry blood from a patient;
   a first pressure detector in line with the venous line;
   a bubble detector in line with the venous line;
   a bubble trap in line with the venous line;
   a blood reservoir that receives blood that has passed through the bubble detector;
   a reservoir return line connecting the blood reservoir to the venous line and configured to return blood to the venous line up-line from the bubble detector;
   a first pump in line with the reservoir return line, between the blood reservoir and the venous line;
   an adjustable blood level detector operably connected to the blood reservoir and the first pump and configured to detect a blood level within the blood reservoir;
   a second pump down-line from the bubble trap;
   a second pressure detector down-line from the second pump;
   an oxygenator down-line from the second pressure detector; and
   an arterial line for transporting blood from the oxygenator back to the patient,
   wherein the first pump is capable of pumping blood from the blood reservoir to the venous line, and
   wherein the adjustable blood level detector is configured such that, when the adjustable blood level detector determines that the blood level within the blood reservoir is below a threshold value, the adjustable blood level detector directs the first pump to reduce or cease operation until the blood level within the blood reservoir reaches an acceptable level.

9. The method according to claim 8, wherein the second pump is an impeller or centrifugal pump.

10. The method according to claim 8, wherein the oxygenator also serves as a heat exchanger capable of heating the blood.

11. The method according to claim 8, wherein the extracorporeal life support device further comprises an occluder clamp on a line connecting the bubble detector and the blood reservoir.

12. The method according to claim 8, wherein the blood reservoir comprises a vacuum regulator that is capable of adjusting the pressure of the blood reservoir.

13. The method according to claim 8, wherein the blood reservoir is self-regulating.

14. The method according to claim 8, wherein the extracorporeal life support device further comprises a suction device line connected to the blood reservoir, and wherein the blood reservoir is capable of receiving blood collected by a suction device and provided through the suction device line during a surgical procedure.

15. The pediatric extracorporeal life support device according to claim 1, wherein the first pump is a roller pump.

16. The method according to claim 8, wherein the first pump is a roller pump.

\* \* \* \* \*